(12) United States Patent
Meerbeck et al.

(10) Patent No.: US 8,603,831 B2
(45) Date of Patent: Dec. 10, 2013

(54) METHOD OF DETERMINING A COMPOSITION OF FUEL IN A POWER STATION

(75) Inventors: Bernhard Meerbeck, Kelkheim (DE); Rainer Speh, Weiterstadt (DE)

(73) Assignee: Siemens Aktiengesellschaft, München (DE)

( * ) Notice: Subject to any disclaimer, the term of this patent is extended or adjusted under 35 U.S.C. 154(b) by 3 days.

(21) Appl. No.: 13/128,453

(22) PCT Filed: Nov. 10, 2009

(86) PCT No.: PCT/EP2009/064872
§ 371 (c)(1),
(2), (4) Date: Jul. 29, 2011

(87) PCT Pub. No.: WO2010/055020
PCT Pub. Date: May 20, 2010

(65) Prior Publication Data
US 2011/0277539 A1    Nov. 17, 2011

(30) Foreign Application Priority Data
Nov. 11, 2008   (DE) .......................... 10 2008 056 675

(51) Int. Cl.
*G01N 33/22*    (2006.01)

(52) U.S. Cl.
USPC ........ 436/137; 73/53.01; 73/61.41; 73/61.76; 73/64.54

(58) Field of Classification Search
USPC ........... 436/171, 137; 73/53.01, 61.41, 61.76, 73/64.54
See application file for complete search history.

(56) References Cited

U.S. PATENT DOCUMENTS 6,361,310 B1 *  3/2002  Fastnacht et al. ............... 431/12
2008/0105175 A1   5/2008  Booth et al.

FOREIGN PATENT DOCUMENTS

| DE | 19509412 C2 | 1/1997 |
|---|---|---|
| DE | 19714073 A1 | 10/1998 |
| WO | WO 9710473 A1 | 3/1997 |
| WO | WO 9939137 A1 | 8/1999 |
| WO | WO 2007062019 A2 | 5/2007 |

* cited by examiner

*Primary Examiner* — Monique Cole

(57) ABSTRACT

A method and a device for monitoring the combustion of fuel in a power station are provided. An actual concentration distribution of a material in a combustion chamber is measured, the actual concentration distribution is evaluated, taking into consideration a combustion stochiometry, and conclusions are drawn regarding a composition of the fuel on the basis of the evaluation that has been carried out.

5 Claims, 1 Drawing Sheet

FIG 1
FIG 2
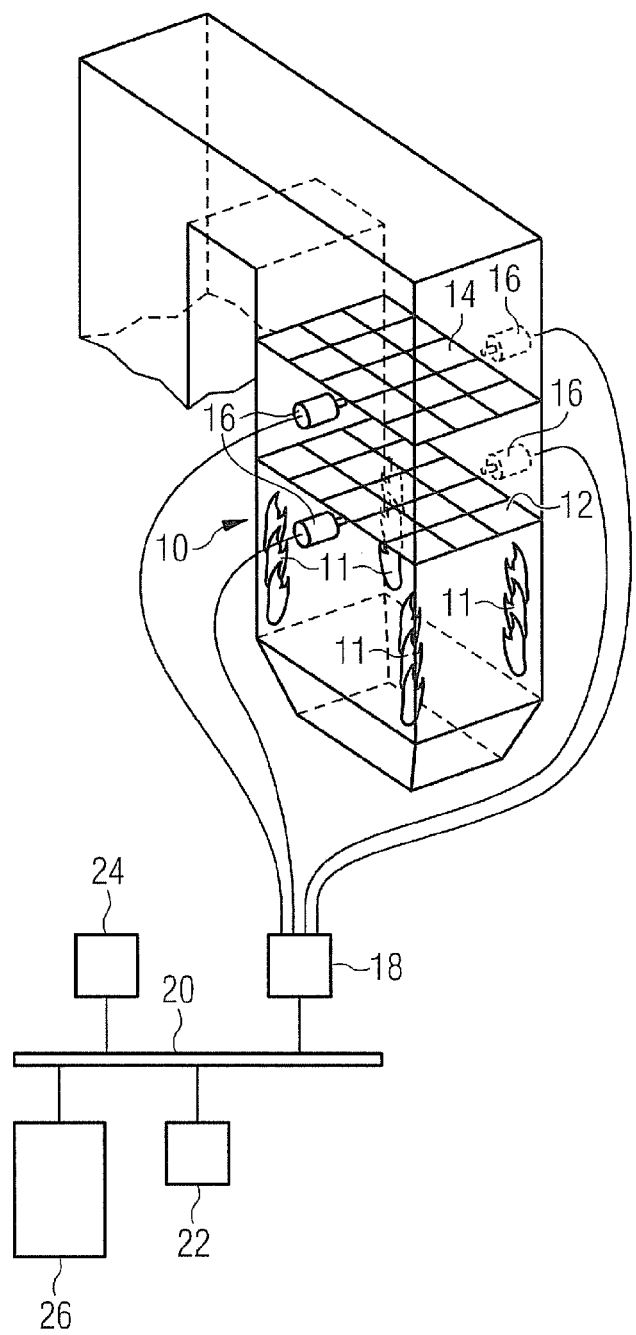
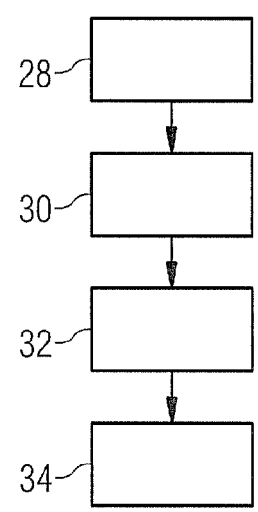

METHOD OF DETERMINING A COMPOSITION OF FUEL IN A POWER STATION

CROSS REFERENCE TO RELATED APPLICATIONS

This application is the US National Stage of International Application No. PCT/EP2009/064872 filed Nov. 10, 2009, and claims the benefit thereof. The International Application claims the benefits of German Patent Application No. 10 2008 056 675.6 DE filed Nov. 11, 2008. All of the applications are incorporated by reference herein in their entirety.

FIELD OF INVENTION

The invention relates to a method and a device for monitoring the combustion of fuel in a combustion chamber in a power station, whereby an actual concentration distribution of a substance in the combustion chamber is measured.

BACKGROUND OF INVENTION

For power stations, the fundamental objective is to monitor the combustion which is taking place in a combustion chamber in the power station, for example a boiler with a base area of 10 meters by 10 meters, over as wide an area as possible, to enable the variables required for optimizing the combustion process to be derived therefrom.

Thus, absorption spectroscopy is a known method. As an alternative measurement technology, acoustic pyrometry is also known. Using absorption spectroscopy or acoustic pyrometry, it is only possible to measure mean values along a line in the boiler or combustion chamber.

For the purpose of calculating the temperature and concentration distribution in a plane in a combustion chamber from measured mean values at various places in a power station's combustion chamber, a known method is the CAT measurement technique, Computer Aided Tomography.

SUMMARY OF INVENTION

An object of the invention is to enable more extensive monitoring of the combustion in a power station, in order thereby to supply the basis for optimizing the combustion process.

The object is achieved by a method and a device as claimed in the independent claims. Advantageous developments are described in the dependent claims.

The method in accordance with the invention for monitoring the combustion of fuel in a combustion chamber in a power station includes the steps: measure an actual concentration distribution of a substance in the combustion chamber, analyze the actual concentration distribution, taking into account the combustion stochiometry, and draw conclusions about the composition of the fuel on the basis of the analysis undertaken.

Correspondingly, the device in accordance with the invention for monitoring the combustion of fuel in a combustion chamber in a power station includes equipment for measuring an actual concentration distribution of a substance in the combustion chamber, equipment for analyzing the actual concentration distribution, taking into account the combustion stochiometry, and equipment for drawing conclusions about the composition of the fuel on the basis of the analysis undertaken.

In other words, the basic idea underlying the invention is that it is possible, by means of a concentration measurement for at least one substance, such as for example a gaseous component of the waste gas from the combustion, to determine a quantitative property of a fuel. It is possible, when the combustion stochiometry is taken into consideration, to determine whether a particular component in the substance under investigation is present in the quantity which it should be on the basis of the combustion stochiometry.

Thus it is advantageously possible, in particular, to effect a quantitative determination of the composition of a fuel, such as coal in particular, on the basis of several measured concentration values for, preferably, the substances $CO_2$ (carbon dioxide), $CO$ (carbon monoxide), $O_2$ (oxygen), $H_2O$ (water) and/or $N_2$ (nitrogen). In doing this, the combustion stochiometry will preferably be used as follows:

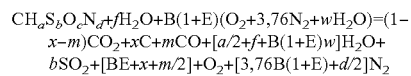

where an excess of air of $\lambda=1+E$ is assumed and the parameters a, b and c are determined by reference to the measured concentrations, while it is preferably assumed for the sake of simplification that $d=0$.

With a first advantageous development of the inventive solution, in making the analysis a mean value is formed in at least one dimension for a measured two-dimensional concentration distribution.

In the case of a second advantageous development of the inventive solution, when the measurements are made a concentration distribution will be determined in each of two planes in the combustion chamber, and to increase the reliability of the measurements a plausibility check will be carried out between these measurements.

In the case of a third advantageous development of the inventive solution, when making the analysis a measured actual temperature distribution will in addition be taken into account. The analysis in accordance with the invention can in this way be safeguarded and refined.

With a fourth advantageous development of the inventive solution, in order to produce a method which is particularly simple in computational terms, when drawing conclusions about the composition of the fuel which is being burned, a concentration distribution determined from a fuel sample, and its combustion stochiometry, will be compared with the measured actual concentration distribution.

With a fifth advantageous development of the inventive solution, when drawing conclusions about the composition of the burning fuel, a comparison is made against at least one saved characteristic concentration distribution of a fuel sample. This makes possible a procedure which is particularly rapid in computational terms.

With a sixth advantageous development of the inventive solution, the drawing of conclusions about the composition of the fuel is effected at the same time as the making of measurements. In summary, it is thus simply possible in a way which is cost-effective, simple and at the same time is a reliable process, to achieve a recognition of the quantitative composition of a fuel which, although only approximated, is on the other hand very up-to-date.

In the above definition of the invention, the term "substance" refers generally to any type of combustion product, in particular in the form of gas as a component of the waste gas. Furthermore, the term fuel is to be understood as any type of material which comes to be burned in power stations. For coal-fired power stations, which are particularly relevant in the present case, these are different coals or different types of coal.

The advantageous developments cited for the inventive method will preferably also be realized in the form of appropriately adapted equipment in the inventive devices.

BRIEF DESCRIPTION OF THE DRAWINGS

An exemplary embodiment of the inventive solution is explained in more detail below by reference to the attached schematic drawings. These show:

FIG. 1 an exemplary embodiment of the inventive device, and

FIG. 2 an exemplary embodiment of the inventive method.

DETAILED DESCRIPTION OF INVENTION

FIG. 1 shows a combustion chamber 10 in a coal-fired power station, which is not shown further here, in which a coal-fired furnace burns when the coal-fired power station is in operation. The combustion chamber 10 then has coal in it as the fuel, with its associated combustion gases, several flames 11 and waste gases.

Provided in the combustion chamber 10 are two measurement planes 12 and 14, on the edges of each of which are measuring instruments 16, spaced apart from each other. In each case, two of the measuring instruments 16 permit measurement along a line in the associated measurement plane, 12 or 14 as applicable, wherein the concentration of the substances $O_2$ (oxygen) and CO (carbon monoxide), for example, can be measured with the help of the measuring instruments 16 and an associated analysis device 18.

Furthermore, using the measuring instruments 16 and the analysis device 18 it is possible to determine the temperature distribution in the associated measurement plane, 12 or 14 as applicable. Here, the measurement is based on a combination of measurement technology and CAT calculation.

The analysis device 18 is coupled operationally via a data bus 20 to an optimization device 22, an operating device 24, and management equipment or control and instrumentation equipment 26. Via the operating device 24, the actual concentration distributions and temperature distributions in the planes 12 and 14, measured by the analysis device 18, can be used in such a way that the optimization device 22 can draw conclusions from them about the quantitative composition of the fuel currently burning in the combustion chamber 10, in the present case the quantitative composition of the coal which is there.

The quantitative composition of the fuel is determined, for example, in order to optimize the flames 11 burning in the combustion chamber 10, in particular in respect of a low emission of $NO_x$ (oxides of Nitrogen).

For the purpose of determining the quantitative composition of the fuel, the optimization device 22 uses or takes into account, as appropriate, the general combustion stochiometry, as reflected in the above formula. For this purpose, the distributions of the concentration and of the temperature which have been actually measured are first averaged along one dimension, in particular in a plane, and are mutually checked for their plausibility.

The associated method is illustrated in FIG. 2. It includes the step 28: measure the concentration distribution of the substances $N_2$, $SO_2$, $CO_2$, $O_2$ and CO and the temperature distribution in the plane 12. In step 30 the concentration distribution of the substances $N_2$, $SO_2$, $CO_2$, $O_2$ and CO in the plane 14, and the temperature distribution there, are measured at the same time.

Concentrations which are not measured can then be determined from the equations for the combustion stochiometry or from measurements at another place.

In doing this, a plausibility check is also carried out in steps 28 and 30 on the concentration distributions determined in the two planes 12 and 14 in the combustion chamber 10, and a mean value is formed over the measured concentrations, which in each case are two-dimensional.

In step 32 the concentration distribution and the temperature distribution in the planes 12 and 14 are, as explained above, analyzed taking into account the combustion stochiometry in such a way that in a step 34 conclusions can be drawn about the quantitative composition of the fuel in the combustion chamber 10.

On the basis of this conclusion, optimization of the combustion is then effected in a step 34, for example by a change in the air layering and/or a section by section change in the excess air.

The invention claimed is:

1. A method of determining a composition of fuel in a combustion chamber of a power station, comprising:
   providing a combustion chamber and a fuel;
   burning the fuel in the combustion chamber;
   measuring an actual concentration distribution of a substance in the combustion chamber;
   analyzing the actual concentration distribution taking into account a combustion stochiometry; and
   determining a composition of the fuel based upon the analyzing of the actual concentration distribution.

2. The method as claimed in claim 1, wherein the combustion chamber comprises two measurement planes,
   wherein in for each measurement plane the actual concentration distribution is measured.

3. The method as claimed in claim 2, wherein each measurement plane comprises measuring instruments,
   wherein the measuring instruments are connected to an analysis device,
   wherein a temperature distribution is measured in each measurement plane using the measuring instruments and the analysis device,
   wherein the temperature distributions and the actual concentration distributions are transmitted to an optimization device which is configured to determine the composition of the fuel burning in the combustion chamber.

4. The method as claimed in claim 1, further comprising:
   comparing a concentration distribution and a combustion stochiometry of a fuel sample with the actual concentration distribution during the determining of the composition of the fuel.

5. The method as claimed in claim 4, wherein the concentration distribution and the combustion stochiometry of the fuel sample have been stored before comparing the fuel sample with the actual concentration distribution.

* * * * *